United States Patent [19]
Gerhart et al.

[11] Patent Number: 4,902,719
[45] Date of Patent: Feb. 20, 1990

[54] 5-SUBSTITUTED ORNITHINE DERIVATIVES

[75] Inventors: Fritz E. Gerhart, Kehl Leutesheim, Fed. Rep. of Germany; Nikolaus J. Seiler, Strasbourg, France

[73] Assignee: Merrell Dow Pharmaceuticals Inc., Cincinnati, Ohio

[21] Appl. No.: 305,247

[22] Filed: Feb. 1, 1989

[30] Foreign Application Priority Data

Feb. 5, 1988 [GB] United Kingdom ............... 88400275

[51] Int. Cl.$^4$ ............................................. A61K 31/195
[52] U.S. Cl. ...................................... 514/564; 562/561
[58] Field of Search ................. 562/561, 574; 514/564

[56] References Cited

U.S. PATENT DOCUMENTS 4,326,071  4/1982  Bey ........................................ 562/561
4,668,703  5/1987  Krantz ................................. 562/561

OTHER PUBLICATIONS

Daune, Biochem. J., 253(2), pp. 481–488 (7/1988).
Bey, J. Neurochem., 37(5), pp. 1341–1344 (1981).

*Primary Examiner*—Michael L. Shippen
*Attorney, Agent, or Firm*—Stephen L. Nesbitt; Michael J. Sayles

[57] ABSTRACT

This invention relates to ornithine derivatives substituted at the 5 position with an R group which can be a $-CH_2F$, $-CHF_2$, $-CHClF$, $-C\equiv CH$, $-CH=CH_2$, or $-CH=C=CH_2$ group and the pharmaceutically acceptable acid addition salts thereof which are specific inhibitors of OAT and can be used in the treatment of conditional deficiencies of ornithine.

9 Claims, No Drawings

5-SUBSTITUTED ORNITHINE DERIVATIVES

FIELD OF THE INVENTION

This invention relates to certain 5-substituted ornithine derivatives, their use in the treatment of ammonia intoxication and in the treatment of other conditional deficiencies of ornithine, their pharmaceutical compositions, and the process of their preparation.

BACKGROUND OF THE INVENTION

Ornithine is metabolically degraded via three pathways. Ornithine is the substrate for the enzyme ornithine decarboxylase (ODC). ODC action on ornithine results in putrescine required for cell growth and division. From a quantitative point of view this pathway is normally quite insignificant but is important in rapidly dividing cells such as tumor cells.

Ornithine is also a substrate for L-Ornithine:2-oxoacid aminotransferase (OAT), a mitochondrial enzyme present in many tissues including liver, kidney, and brain. It catalyzes the transamination of L-ornithine (Orn) to 2-oxoglutarate, producing glutamic γ-semialdehyde and glutamate. The liver enzyme is believed to function in the intracellular production of proline and the shuttling of carbon skeletons from excess dietary amino acids to the tricarboxylic acid cycle and it has been suggested that OAT competes with ornithine transcarbamylase for Orn and thus limits urea cycle activity. Inhibition of this enzyme can result in an excess of ornithine.

Ornithine is also the substrate for ornithine carbamoyltransferase (OCT), an enzyme of the urea cycle responsible for the conversion of ornithine to citrulline.

While ornithine is not normally considered an essential amino acid, certain conditions can arise naturally or can result from therapeutic intervention which produce a relative conditional efficiency of ornithine, for example, hepatic toxicity or failure, gastrointestinal hemorrhage, inherited urea cycle disorders, pregnancy, and malnutrition. In these instances, ornithine is rate limiting for urea cycle function. Administration of ornithine is largely ineffective because of the action of OAT, but inhibition of this enzyme would result in additional amounts of ornithine available for urea cycle function.

Various inhibitors of OAT are known. L-Canaline (2-amino-4-aminooxybutyric acid), for example, a naturally occurring structural analogue of Orn, forms an oxime with pyridoxalphosphate and affects a series of pyridoxalphosphate dependent enzymes. Because of this oxime formation, the biochemical effects of L-canaline can not be convincingly attributed to the inhibition of OAT.

Because of the structural analogy between Orn and 4-aminobutyric acid (GABA), and the analogous reaction mechanisms of OAT and 4-aminobutyric acid:2-oxoacid aminotansferase (GABA-T), some enzyme-activated irreversible inhibitors of GABA-T, such as 4-aminohex-5-ynoic acid and 5-amino-1,3-cyclohexadienylcarboxylic acid (gabaculine), are also potent irreversible inhibitors of OAT, but, by definition, are not specific for this enzyme.

The 5-substituted ornithine derivatives of this invention are the first known specific irreversible inhibitors of L-ornithine:2-oxoacid aminotransferase (OAT). When administered, the ornithine derivatives of this invention inhibit the transformation of L-ornithine to glutamic acid semialdehyde and thus cause an increase in ornithine concentration which would then be available to enhance urea cycle function in liver. As such, the compounds of this invention are useful in the treatment of conditional deficiencies of ornithine.

SUMMARY OF THE INVENTION

This invention relates to 5-substituted ornithine derivatives of the formula:

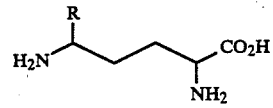

wherein R is a —CH$_2$F, —CHF$_2$, —CHClF, —C≡CH, —CH=CH$_2$, or —CH=C=CH$_2$ group and the pharmaceutically acceptable acid addition salts thereof, their use in the treatment of conditional deficiencies of ornithine, their pharmaceutical compositions, and their preparation.

DETAILED DESCRIPTION OF THE INVENTION

The compounds of this invention are ornithine derivatives wherein the 5-position has been substituted with various organic groups and include 2,5-diamino-6-fluoohexanoic acid (δ-fluoromethylornithine;

2,5-diamino-6,6-difluorohexanoic acid (δ-difluoromethylornithine);

2,5-diamino-6-chloro-6-fluorohexanoic acid (δ-chlorofluoromethylornithine);

2,5-diaminohept-6-ynoic acid (δ-acetenylornithine);

2,5-diaminohept-6-enoic acid (δ-vinylornithine); and 2,5-diamino-6,7-octadienoic acid (δ-allenylornithine).

The 5-substituted ornithine derivatives of this invention are useful both in the free amino acid form and in the form of their acid addition salts. The acid addition salts are simply a more convenient form for use and, in practice, use of the salt amounts to use of the equivalent quantities of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, α-ketoglutaric, α-ketocaproic, α-ketoisocaproic, α-ketoisovaleric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. With organic acids only the monoacid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free amino acid in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

The compounds of this invention contain two chiral centers at the 2 and 5 positions of the corresponding ornithine. The chiral centers of the compounds of this invention are indicated by an adjacent asterisk (*) in the structural formula as follows:

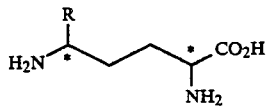

The two chiral centers in the compounds of this invention provide for two diastereomeric pairs of compounds or four enantiomeric compounds. In principle, the compounds of this invention could be physically separated into two diastereomeric pairs of compounds which would require optical resolution to further separate the mixture into the four individual enantiomers. While one or more of the individual enantiomer of a compound of this invention may possess little or no biological activity and the observed activity of the substituted ornithine derivatives of formula may be due to, for example, only one of the diastereomers, in practice, administration of a mixture of the diastereomers is effective.

The 5-substituted ornithines of structure 1 wherein R is —CHF$_2$, —CH$_2$F, or —CHClF can be prepared by the reaction of an acetonitrile derivative of the following formula 2:

wherein R is —CHF$_2$, CH$_2$F, or —CHClF with a Grignard reagent prepared from an hydroxy-protected 3-hydroxypropyl halide of formula 3, and subsequent reduction with sodium borohydride:

wherein P is an hydroxy protecting group and X is a chloro, bromo, or iodo group. Any hydroxy protecting group stable to the Grignard reaction conditions and which is readily removed can be used, for example, a benzyl group or a tetrahydropyranyl (THP) group. The compound of formula 3 wherein P is a benzyl group and X is a chloro group can be prepared by, for example, adding a slight molar excess of a nonnucleophilic base such as potassium or sodium t-butoxide to a 1:1 molar mixture of benzyl bromide and 3-chloropropanol. Preferably a solvent such as tetrahydrofuran (THF) is used to facilitate the reaction. The temperature of the mixture is preferably kept below about 15° C. during the period of reactant addition but may conveniently be maintained at room temperature, 25° C., after the addition is complete. The reaction mixture is then allowed to react for from 1 to 20 hours, preferably about 8 to 12 hours and subsequently about 1 equivalent of an acid such as hydrochloric acid (1 N) is added to the mixture, preferably dropwise. The formula 3 compound can then be isolated in any suitable manner such as by extraction of the reaction with ethyl ether and subsequent solvent removal from the organic phase solution.

The amine group of the resulting product of the Grignard reaction/sodium borohydride reduction, the fluorinated amine of structure 4,

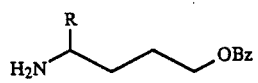

wherein R is —CHF$_2$, —CH$_2$F, or —CHClF and Bz is a benzyl group, is then protected by, for example, conversion to its phthalamide derivative of structure 5

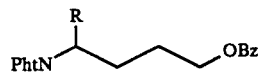

wherein R is —CHF$_2$, —CH$_2$F, or —CHClF group, Bz is a benzyl group, and NPht is a phthalimide protected amino group. The phthalimide derivative can be formed by, for example, treatment of the structure 4 fluorinated amine with a benzene solution of N-carbethoxyphthalimide. The resulting intermediate product is then allowed to react with triethylamine in, for example, a dichloromethane solution, to form the desired phthalimide protected amine.

The benzyl protecting group is then removed to form the intermediate, corresponding alcohol of structure 5a

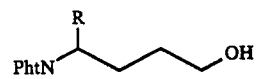

by, for example, catalytic hydrogenation employing hydrogen gas at atmospheric pressure and a Palladium on carbon catalyst, and the resulting free hydroxy group is oxidized to the corresponding aldehyde of structure 6

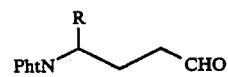

wherein R is a —CHF$_2$, —CH$_2$F, or —CHClF group. The oxidation of the alcohol group can be accomplished by, for example, use of the Swern oxidation reaction in the following manner. A slight molar excess of dimethylsulfoxide (DMSO) in dichloromethane solution is added to a cooled (e.g., −60° C.) solution of about 0.6 molar equivalents of oxalylchloride, (COCl)$_2$, in dichloromethane. Subsequently the alcohol is added and the mixture stirred for about 1 hour, at which time a solution of triethylamine in dichloromethane is added, the resulting mixture cooled to about −10° C., and allowed to react until complete. The reaction mixture is then quenched with water. Isolation of the product from the mixture can be accomplished in the usual manner. The structure 6 aldehyde is then reacted with vinyl magnesium bromide to produce the vinyl alcohol derivative of structure 7

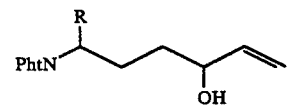

wherein R is a —CHF₂, —CH₂F, or —CHClF group. This Grignard reaction is carried out in the usual manner in, for example, THF solution at reduced temperature, such as from −40° C. to about 0° C..

The alcohol group of the vinyl alcohol derivative of structure 7 is then transformed into a phthalimide group to produce the diphthalimide derivative of structure 8

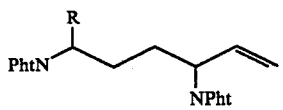
8 wherein R is a —CHF₂, —CH₂F, or —CHClF group. This can be accomplished by, for example, adding a solution of a slight molar excess of diethylazodicarboxylate (DEAD) in THF to a mixture of about 1 molar equivalent of triphenylphosphine, a slight molar excess of phthalimide and the vinyl alcohol derivative of structure 7. The solution is kept cooled (i.e., <20° C.) and allowed to react for about 3 days after which extractive work up in the usual manner gives the desired diphthalimide derivative.

The diphthalimide of structure 8 is then used to prepare the carboxylic acid of structure 9

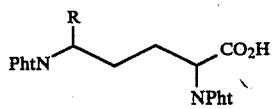
9 wherein R is a —CHF₂, —CH₂F, or —CHClF group by potassium permanganate oxidation of the vinyl group in the usual manner. The phthalimide protecting groups of the acid (9) are removed by simple acid hydrolysis to produce the desired free diamine of structure 1 wherein R is a —CHF₂, CH₂F, or —CHClF group by, for example, allowing the diphthalimide protected acid to react with hydrochloric acid in acetic acid solution for about 2 days at the reflux temperature of the mixture.

The more stable dihydrochloride salt can be prepared from the free amino acid by first preparing the di-t-butyloxycarbonyl (diBOC) derivative of structure 9a

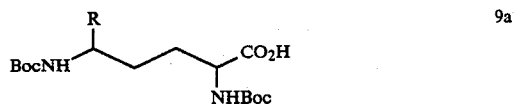

by, for example, allowing the free amino acid to react with t-butyloxycarbonyl anhydride and triethylamine in aqueous THF. Subsequent treatment of the diBOC derivative with hydrochloric aid in ethyl ether for, for example, 3 days gives the dihydrochloride salt of the desired compound of structure 1 wherein R is a —CHF₂, —CH₂F, or —CHClF group.

The 5-substituted ornithines of structure 1 wherein R is —CH=CH₂ are prepared as illustrated in Scheme A.

SCHEME A

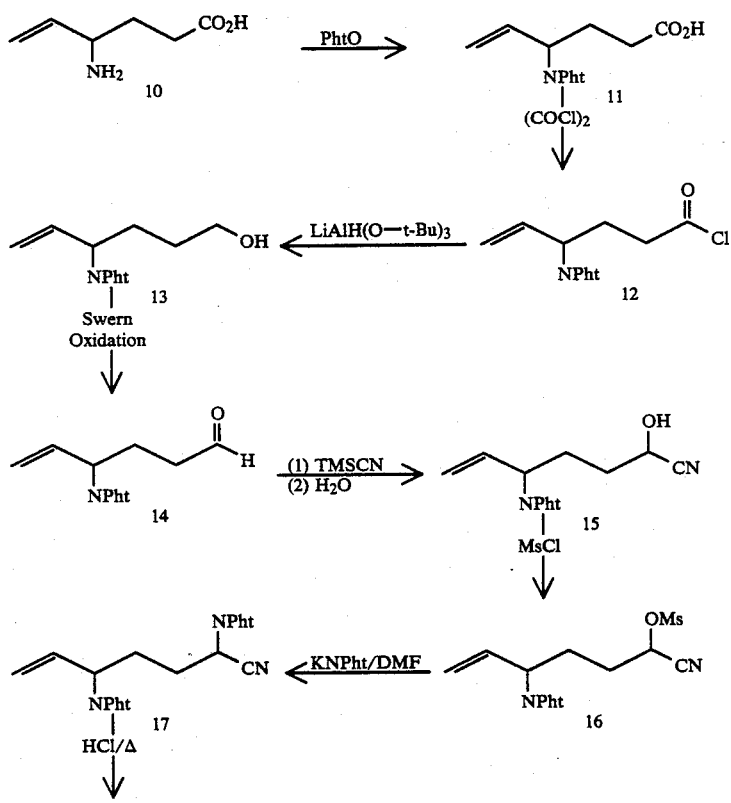

SCHEME A

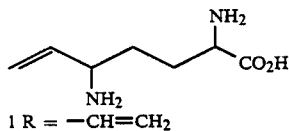

1 R = —CH=CH₂

Vinyl-GABA (10) is transformed into its N-phthaloyl derivative (11) by heating with phthalic anhydride in toluene. Reaction with oxalyl chloride in THF and catalytic pyridine gives the acid chloride (12) which is reduced to the alcohol (13) by reaction with 2 equivalents of lithium-tris-tert-butoxy-aluminiumhydride in THF. Swern oxidation using dimethyl sulfoxide (DMSO) and oxalyl chloride gives the aldehyde (14) which is then converted to the cyanohydrine (15) by reaction with trimethylsilylcyanide and subsequent hydrolysis. The mesylate (16) prepared in the usual manner by reaction with mesyl chloride (MsCl) is then allowed to react with potassium phthalimide (KNPht) in dimethylformamide (DMF) solution to give 17 which upon hydrolysis results in production of the desired δ-vinylornithine (1, R=—CH=CH₂).

The compounds of structure 1 wherein R is a —C≡CH or —CH=C=CH₂ group can be prepared in analogy to scheme A from δ-acetenyl GABA and δ-allenyl GABA, respectively, or they can be prepared from δ-vinylornithine (1, R=—CH=CH₂) as illustrated in Scheme B.

in toluene to form the cyclized amine (19); and (c) treatment with di-tert-butyldicarbonate (BOC₂O). The N-protected lactam is transformed into the acetylenic lactam (22) by treatment with molecular bromine in carbon tetrachloride (CCl₄) to form a dibromo intermediate (21) which upon treatment with about 5 equivalents of potassium-t-butoxide at reduced temperature, i.e. —60° C., in THF results in the desired lactam. Subsequent reaction with a mixture of 37% aqueous formaldehyde, copper(I)bromide, and diisopropylamine in dioxane results in the allenic lactam (23). Subsequent deprotection by treatment with, for example, hydrogen chloride gas in diethyl ether and hydrolysis by treatment with refluxing 2 N hydrochloric acid of either the acetylenic or allenic lactams gives δ-acetenylornithine or δ-allenylornithine, respectively. The compounds of this invention are inhibitors of OAT and can be useful in treating any disease or condition characterized by a conditional deficiency of ornithine. The effectiveness or the compounds of this invention to treat conditional deficiencies of ornithine can be demonstrated by their ability to antagonize ammonia intoxication by, for example, the method reported in L. Zieve, Journal of the American College of Nutrition, Volume 5, pages 167–176 (1986). The term "patient" as used herein is

SCHEME B

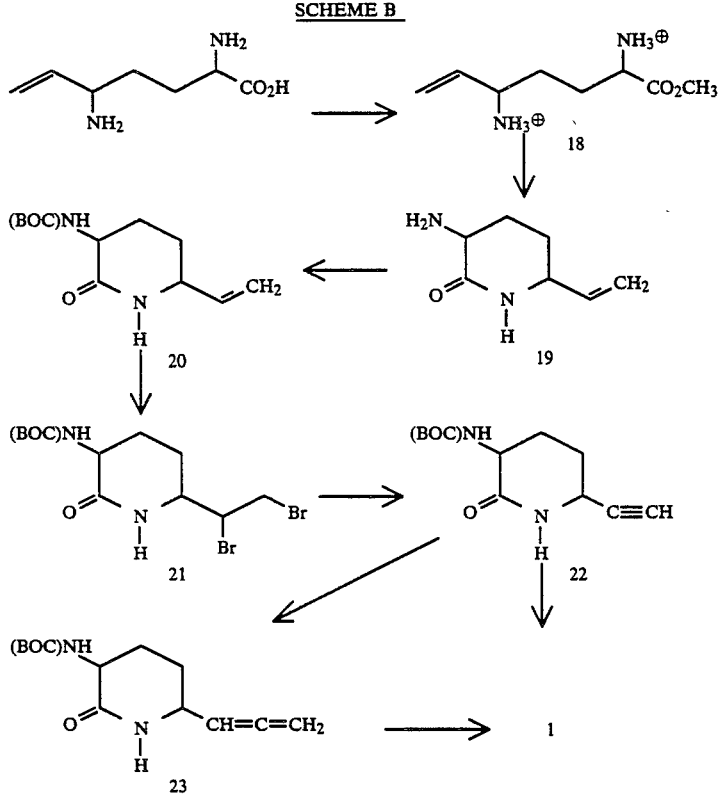

Delta-vinylornithine is converted to the N-protected lactam (20) in three steps by (a) heating to reflux with thionyl chloride (SOCl₂) in methanol to give the ammonium salt (18); (b) liberation of the free base by treatment with a base such as sodium carbonate and heating taken to mean mammals such as primates, including humans, sheep, horses, bovine cows and bulls, pigs, dogs, cats, rats and mice.

The quantity of δ-substituted ornithine derivative of this invention administered will vary depending on the patient, mode of administration, severity of the disease or condition and can be any effective amount. Repetitive daily administration of the δ-substituted ornithine derivative is desirable. The effective amount of a δ-substituted ornithine derivative of this invention can be from about 0.001 mg/kg to about 10 mg/kg of patient body weight per day. Preferably the δ-substituted ornithine derivative will be administered in unit dosage form from one to four doses per day of from, for example, 10 mg per dose.

The preferred route of administration for the δ-substituted ornithine derivatives of this invention is oral administration. For oral administration the δ-substituted ornithine derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The δ-substituted ornithine derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures The parenteral compositions of this invention will typically contain from about 0.5 to about 25% by weight of the ornithine derivative of formula 1 in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLE 1

PREPARATION OF
6-FLUORO-2,5-DIAMINOHEXANOIC ACID
DIHYDROCHLORIDE

The title compound was prepared from n-chloropropanol and fluoroacetonitrile (2, R=—CH$_2$F) in the following manner.

A. Preparation of 3-benzyloxypropylchloride

To a stirred solution of sodium tertiobutoxide (421 g, 4.4 mol) in dry tetrahydrofuran (4 L), under nitrogen, was added a mixture of benzyl bromide (718 g, 4.2 mol) and n-chloropropanol (396 g, 4.2 mol). The temperature was maintained <15° C. The mixture was stirred overnight at room temperature. Acidification with 2 N HCl was followed by extractions with ether (3×1 L). The ether layer was separated, washed with water, dried over Na$_2$SO$_4$ and evaporated. The residue was distilled (76–86° C./0.03 mm Hg). The title compound (3, R=—CH$_2$F) was obtained as a colorless oil: 619 g (80%). NMR (H$^1$, CDCl$_3$, 90 MHz).

B. Preparation of 5-benzyloxy-2-aminofluoropentane

A solution of 3, (R=—CH$_2$F) (476 g, 2.58 mol) in dry ether (2.4 L) was added slowly to magnesium turnings (125 g, 5.2 mol) under nitrogen at such a rate to maintain a gentle reflux[1]. The reaction was then refluxed for 3 hours and left standing overnight. The mixture was filtered under nitrogen and was cooled to −50° C. A solution of fluoroacetonitrile (127 g, 2.15 mol) in dry ether (100 mL) was added dropwise over 30 min., and was stirred 2 hours at −45° C. The reaction mixture was cooled to −60° C., and was added slowly to a precooled solution of sodium borohydride (102 g, 2.76 mol) in methanol (6.5 L) and water (130 mL) at −60° C. The solution was allowed to warm up to −20° C., and 6 N hydrochloric acid (1.5 L) was added, keeping the reaction <−20° C. The addition was very exothermic. The solution was evaporated, the residue was dissolved in water (3 L) and extracted with ether (2 L). The aqueous phase was separated, basified with 10 N NaOH and extracted with ether (3×1.5 L), the ether phase was washed with brine, dried over $Na_2SO_4$, and evaporated to give the title compound (4, R=—$CH_2F$) as a yellow oil: 276 g (50.7%). NMR ($H^1$, $CDCl_3$, 90 MHz).

NOTE: 1. During the addition, the solution was heated at 45° C. to maintain the reflux.

C. Preparation of 5-benzyloxy-2-phthalimido-1-pentane

To a solution of 4, (R=—$CH_2F$) (276 g, 1.31 mol) in benzene (1.2 L) was added a solution of n-carbethoxyphthalimide (260 g, 1.18 mol) in benzene (1.2 L). The mixture was left overnight at room temperature. Whereupon some compound crystallized, the mixture was evaporated. The residue was dissolved in dichloromethane (3 L) and triethylamine (155 g, 1.53 mol) was added. After stirring overnight, the solution was washed with 2 N HCl (1 L) then with water (2×2 L) and evaporated to afford an oil (460 g) which was purified by flash chromatography on 2 kg $SiO_2$. Elution with ethylacetate/petroleum ether 20/80 afforded the title compound (5, R=—$CH_2F$) as an oil: 200 g (45%). NMR ($H^1$, $CDCl_3$, 60 MHz).

D. Preparation of 5-fluoro-4-phthalimidopentanol

A solution of 5, (R=—$CH_2F$) (197 g, 0.58 mol) in absolute ethanol (1.2 L) was hydrogenated at atmospheric pressure over palladium on charcoal (22 g) for 3 days. The catalyst was filtered, the solution was evaporated. The title compound (5a, R=—$CH_2F$) was obtained as an oil: 144 g (100%). NMR ($^1H$, $CDCl_3$, 90 MHz).

E. Preparation of 5-fluoro-4-phthalimidopentanal

To a solution at −60° C. of oxalylchloride (75.3 g, 0.59 mol) in dry dichloromethane (2 L) under nitrogen, was added a solution of dry DMSO (89.1 g, 1.14 mol) in dry dichloromethane (2 L). 5-Fluoro-4-phthalimidopentanol, 5a, (R=—$CH_2F$) (135 g, 0.54 mol) in $CH_2Cl_2$ (2 L) was then added over 15 min. The mixture was stirred 45 min. at −60° C., a solution of triethylamine (352 g, 3.47 mol) in dry $CH_2Cl_2$ (2 L) was added slowly (exothermic). The solution was stirred overnight, cooled to −10° C. and water (2 L) added. The organic phase was separated, washed with 4 N HCl, followed by water (3×2 L). The organic phase was separated, dried over $Na_2SO_4$ and evaporated. The residue was dissolved in ether, washed with water (3×0.5 L) and dried over $Na_2SO_4$. Evaporation of the ether phase gave an oil which was heated at 70° C./0.1 mm Hg to remove traces of DMSO. The title compound (6, R=—$CH_2F$) was obtained as a red oil: 136 g (100%). NMR ($^1H$, $CDCl_3$, 90 MHz).

F. Preparation of 3-hydroxy-7-fluoro-6-phthalimidoheptene

To a solution of 6 (R=—$CH_2F$) (136 g, 0.54 mol) in dry tetrahydrofuran, under nitrogen, was added dropwise a solution of vinylmagnesium bromide (633 mL, 0.59 mol) in dry THF at −78° C. After completion of addition, the green solution was allowed to warm to −50° C., the solution was then cooled to −70° C. and a saturated ammonium chloride solution (2 L) was added. The temperature rose to −40° C. and a white solid was precipitated. The mixture was left standing overnight, the two layers were separated, the aqueous phase was extracted with ether (2×1 L). The organic phase was washed with brine, dried over $Na_2SO_4$, and evaporated to give a yellow oil (147 g) which was dissolved in THF and stirred 3 hours with saturated sodium bisulfite solution. The organic phase was separated, evaporated, and the residue was dissolved in ether and was washed with brine, the ether layer was separated, dried over $Na_2SO_4$ and evaporated to give an oil (133 g). A filtration through silica gel, elution with petroleum ether/ethyl acetate (1:1), afforded the title compound (7, R=—$CH_2F$) as an oil: 133 g (88%). TLC PE/EtOAc 1:1, 2 spots, Rf (product)-0.4. NMR ($^1H$, $CDCl_3$, 90 MHz).

G. Preparation of 7-fluoro-3,6-bisphthalimidoheptene

To a solution of triphenylphosphine (103 g, 0.39 mol), phthalimide (57.8 g, 0.43 mol) and 3-hydroxy-7-fluoro-6-phthalimidoheptene (109 g, 0.39 mol) in dry THF (2 L) under nitrogen, was added dropwise a solution of diethylazodicarboxylate (75.4 g, 0.43 mol) in dry THF (1 L). The solution was kept <20° C. The reaction mixture was stirred for 72 hours. The THF layer was separated and evaporated to give an oil which was boiled in water (5×250 mL), the water was decanted and the residue was dissolved in dichloromethane. After washing with water, the organic phase was separated, dried over $Na_2SO_4$ and evaporated to eliminate triphenylphosphine oxide. Evaporation of the ether phase and chromatography of the residue (200 g) on silica gel (1.5 kg), elution with petroleum ether/ethyl acetate (2:3) afforded the title compound (8, R=—$CH_2F$) as a white solid: 36.4 g (22.8%). TLC PE/EtOAc 1:1, Rf=0.78. NMR ($^1H$, $CDCl_3$, 90 MHz).

H. Preparation of 6fluoro-2,5-bis-phthalimidohexanoic acid

To a solution of potassium permanganate (41.3 g, 260 mmol) in water (1.1 L) and acetic acid (360 mL) at 0° C., was added dropwise a solution of 8 (R=—$CH_2F$) (36 g, 88.7 mmol) in acetone (1 L). Upon completion of addition, the solution was stirred overnight at room temperature. The solution was cooled to 0° C., and a saturated solution of sodium bisulphite was added dropwise keeping the temperature <5° C. A decolorization with charcoal followed by ether extractions (2×200 mL) then dichloromethane (200 mL) afforded an organic phase which was washed with water, dried ($Na_2SO_4$) and evaporated; the residue was azeotroped with toluene, stirred in acetone, filtered, and was evaporated to give the title compound (9, R=—$CH_2F$) as a white solid: 24 g (64%). NMR ($^1H$, acetone $D_6$, 90 MHz).

I. Preparation of 6-fluoro-2,5-bis-(t-butylcarbamoyl)-hexanoic acid

A solution of 9, (R=—$CH_2F$) (23.5 g, 55.5 mmol) in a mixture of concentrated hydrochloric acid 175 mL) and acetic acid (75 mL) was refluxed for 48 hours. The solution was evaporated, the residue was stirred with water (100 mL), phthalic acid was removed by filtration and the aqueous solution was evaporated to afford the diamine dihydrochloride as a red oil (13 g, 99%). A solution of the diamine dihydrochloride (13 g, 55 mol) di-t-butylcarbonate (42.5 g, 195 mmol) and triethylamine (39.3 g, 390 mmol) in tetrahydrofuran (250 mL) and water (125 mL) was stirred for 48 hours at room temperature and 4 hours at 45° C. The solution was extracted with ether (250 mL) then with dichloromethane (2×150 mL). The combined organic phases were extracted with a sodium bicarbonate solution. The basic water phase was acidified with 1 N hydrochloric acid and then extracted with dichloromethane (3×150 mL), the organic phase was dried over Na₂SO₄ and evaporated to afford 3 g of the title compound (9a, R=—CH₂F) as a white solid. All the water phases were saturated with sodium chloride, extracted with dichloromethane (3×150 mL), dried over sodium sulfate and evaporated to give an oil (21 g). The oil was triturated with petroleum ether to give a slightly brown solid (7.5 g). The two batches were similar in TLC: PE/EtOAc (1:1), R=0.6. Yield: 10.5 g (52%). NMR ($^1$H, CDCl₃, 90 MHz).

J. Preparation of 6-fluoro-2,5-diaminohexanoic acid dihydrochloride

A solution of 9a, (R=—CH₂F) (10.5 g, 28.8 mmol) in anhydrous ether was stirred during 3 days with etherial hydrogen chloride under nitrogen. The suspension was filtered to give a light brown solid, which was charcoaled in water. The solution was evaporated and the residue was triturated with anhydrous ether, collected, stirred with dry acetone to give the title compound (10, R=—CH₂F) as a white powder after filtration under argon. The compound was very hydroscopic. Yield: 4.7 g (69%). C, H, N correct, m.p. 146° C., NMR compatible.

EXAMPLE 2

Tablets are prepared each having the composition:

| | |
|---|---|
| 2,5-diamino-6,6-difluorohexanoic acid | 250 mg |
| starch | 40 mg |
| talc | 10 mg |
| magnesium stearate | 10 mg |

EXAMPLE 3

Capsules are prepared each having the composition:

| | |
|---|---|
| 2,5-diamino-6-fluorohexanoic acid | 400 mg |
| talc | 40 mg |
| sodium carboxymethylcellulose | 40 mg |
| starch | 120 mg |

EXAMPLE 4

Injectable dosages forms are prepared each having the composition:

| | |
|---|---|
| 2,5-diamino-6,6-difluorohexanoic acid | 0.500 g |
| polyoxyethylene sorbitan monooleate | 2.000 g |
| sodium chloride | 0.128 g |
| water for injection qs ad | 20.000 ml |

We claim:
1. A δ-substituted ornithine derivative of the formula:

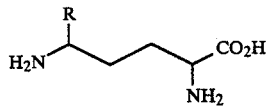

wherein R is a —CH₂F, —CHF₂, —CHClF, —C≡CH, —CH=CH₂, or —CH=C=CH₂ group or a pharmaceutically acceptable acid addition salt thereof.

2. A δ-substituted ornithine derivative of claim 1 wherein R is a —CH₂F group.

3. A δ-substituted ornithine derivative of claim 1 wherein R is a —CHF₂ group.

4. A δ-substituted ornithine derivative of claim 1 wherein R is a —CH=CH₂ group.

5. A method of treating a conditional deficiency of ornithine which comprises administering to a patient in need thereof a therapeutically effective amount of a δ-substituted ornithine derivative of the formula:

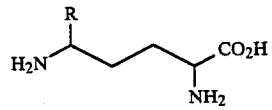

wherein R is a —CH₂F, —CHF₂, —CHClF, —C≡CH, —CH=CH₂, or —CH=C=CH₂ group or a pharmaceutically acceptable acid addition salt thereof.

6. A method of claim 5 wherein the R group of the δ-substituted ornithine derivative is a —CH₂F group.

7. A method of claim 5 wherein the R group of the δ-substituted ornithine derivative is a —CHF₂ group.

8. A method of claim 5 wherein the R group of the δ-substituted ornithine derivative is a —CH=CH₂ group.

9. A pharmaceutical composition for treating conditional deficiencies of ornithine which comprises a δ-substituted ornithine derivative of the formula:

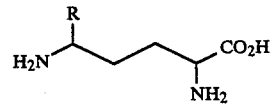

wherein R is a —CH₂F, —CHF₂, —CHClF, —C≡CH, —CH=CH₂, or —CH=C=CH₂ group or a pharmaceutically acceptable acid addition salt thereof and a pharmaceutically acceptably carrier.

* * * * *